United States Patent [19]

Fazio

[11] Patent Number: 5,034,536
[45] Date of Patent: Jul. 23, 1991

[54] PROCESS FOR PREPARING 2-ISOPROPENYL OXAZOLINE

[75] Inventor: Michael J. Fazio, Midland, Mich.

[73] Assignee: The Dow Chemical Company, Midland, Mich.

[21] Appl. No.: 542,671

[22] Filed: Jun. 22, 1990

Related U.S. Application Data

[63] Continuation of Ser. No. 154,530, Feb. 25, 1988, abandoned.

[51] Int. Cl.$^5$ ............................................. C07D 263/10
[52] U.S. Cl. .................................... 548/239; 564/137; 564/208
[58] Field of Search ................. 548/239; 564/137, 208

[56] References Cited

U.S. PATENT DOCUMENTS

| | | | |
|---|---|---|---|
| 2,831,858 | 1/1958 | de Benneville et al. | 548/239 |
| 2,897,182 | 7/1959 | de Benneville et al. | 526/260 |
| 3,312,714 | 4/1957 | Eisenbraun | 548/239 |
| 3,562,263 | 2/1971 | Litt et al. | 544/88 |
| 3,678,065 | 7/1972 | Frump | 548/239 |
| 3,681,329 | 8/1972 | Litt et al. | 544/88 |
| 3,681,333 | 8/1972 | Litt et al. | 544/88 |
| 3,907,893 | 9/1975 | Parker | 564/137 |
| 3,962,270 | 6/1976 | Arlt | 548/239 |
| 4,045,447 | 8/1977 | Arlt | 548/238 |
| 4,148,802 | 4/1979 | Watts, Jr. et al. | 548/239 |
| 4,203,900 | 5/1980 | Kaiser | 548/239 |
| 4,228,102 | 10/1980 | Besecke | 564/208 |
| 4,288,390 | 9/1981 | McDonald | 564/208 |
| 4,354,029 | 10/1982 | Kaiser et al. | 548/239 |
| 4,675,442 | 6/1987 | Besecke | 564/138 |

FOREIGN PATENT DOCUMENTS

| | | | |
|---|---|---|---|
| 49-92013 | 12/1974 | Japan. | |
| 51-34155 | 3/1976 | Japan. | |
| 52-19661 | 2/1977 | Japan. | |
| 61-045793 | 1/1986 | Japan | 564/208 |
| 61-045794 | 1/1986 | Japan | 564/208 |
| 61-129468 | 4/1986 | Japan | 564/208 |
| 89-08099 | 9/1989 | PCT Int'l Appl. | 564/137 |
| 1099657 | 1/1968 | United Kingdom. | |

OTHER PUBLICATIONS de Benneville et al., *J. Org. Chem.*, vol. 23 (1958) pp. 1355-1357.
Tomalia, *Functional Monomers*, vol. 2 (1974) pp. 71-89.
Sanui et al., *Journal of Polymer Science*, Part A-1, vol. 6 pp. 1195-1207.
Ogata et al., *Journal of Polymer Science*, Part A-1, vol. 7 pp. 2847-2858.
Khitrin et al., *Acylation of ethanolamine*, A. A. Zhdanov Gorkovsky Polytechnical Institute, vol. 26 p. 765 (1983).
"The Alkanolamines Handbook" Dow, Midland, Michigan, 1980, pp. 35, 39, 43-49.
Chem. Abst. vol. 82, Entry 139410v (1975) abstracting USSR 453,394.
Chem. Abstr. vol. 82 Entry 155409g (1975) abstracting, Kosai, Japan Kokai 7492013 (1974).
Chem. Abstr. vol. 70 Entry 105875n (1969) abstr. Korshunoz, Zh. Org. Chem. 1969 5(2) 254-262.

*Primary Examiner*—Donald G. Daus

[57] ABSTRACT

Unsaturated esters with an alkyl group at the 2 carbon, such as methyl methacrylate, react with $\beta$-aminoalkanols, such as 2-aminoethanol, in the presence of an alkali metal alkoxide or hydroxide such as sodium methoxide, under moderate temperatures to form an amide such as N-(2-hydroxyethyl)methacrylamide. The amide may be cyclized by a weak Lewis acid, such as ferric chloride, at about 220° C. to form a 2-alkenyl oxazoline, such as isopropenyl oxazoline.

22 Claims, No Drawings

PROCESS FOR PREPARING 2-ISOPROPENYL OXAZOLINE

CROSS-REFERENCE TO RELATED APPLICATION

This is a continuation of application Ser. No. 154,530 filed Feb. 25, 1988 now abandoned.

BACKGROUND OF THE INVENTION

The present invention pertains to the synthesis of unsaturated amides and 2-alkenyl oxazolines.

2-Isopropenyl oxazoline and the related 2-vinyl oxazolines are a class of known compounds whose properties, synthesis and utilities are described in Tomalia, "Reactive Heterocyclic Monomers", 2 *Functional Monomers* 71–89 (R. Yocum & E. Nyquist Ed. 1974). 2-vinyl oxazolines can be polymerized to form poly-2-vinyl oxazolines, which are hydrolyzed to form useful ion-exchange resins.

Three references by de Benneville et al. disclose that 4,4-alkyl-2-vinyl- and 4,4-alkyl-2-isopropenyl oxazolines are prepared by the reaction of an aminoalkanol with acrylic or methacrylic acid in the presence of alkyl titanate or aluminum alkoxides. de Benneville et al., *Oxazine and Oxazoline Derivatives*, U.S. Pat. No. 2,831,858 (Apr. 22, 1958): de Benneville et al., *Oxazine and Oxazoline Polymers*, U.S. Pat. No. 2,897,182 (July 28, 1959): de Benneville et al., "Transesterification of Methyl Methacrylate with Aminoalcohols. Preparation of Primary Aminoalkyl Methacrylate and 2-Isopropenyl-4,4-dimethyl Oxazoline", 23 *J. Org. Chem.* 1355 (1958). The process reported in those references is not functional unless the aminoalkanol contains two alkyl substituents bonded to the carbon which bears the amine group. The process, therefore, can only form 4,4-disubstituted oxazolines. The disubstituted oxazolines do not hydrolyze as effectively as unsubstituted oxazolines. The description of the process shows that alkali metal alkoxides are not effective catalysts for the process shown.

Two references disclose that 2-vinyl oxazoline can be formed by the reaction and subsequent pyrolysis of 1,2-dicyanocyclobutane with two equivalents of an aminoethanol. Arit, *Process for Preparing 2-Vinyl Oxazolines*, U.S. Pat. No. 3,962,270 (June 8, 1976): Arit, *Process for Preparing 2-Vinyl Oxazolines*, U.S. Pat. No. 4,045,447 (Aug. 30, 1977).

It is also known to prepare 2-ethyl oxazoline by first amidating propionic acid with ethanolamine and second dehydrating the resulting amide in the presence of a catalyst. Kaiser, *Process for Preparing 2-Oxazolines*, U.S. Pat. No. 4,203,900 (May 20, 1980). The resulting ethyl oxazoline is converted by reaction with formaldehyde to 2-(1-hydroxyisopropyl) oxazoline. That intermediate can be converted to isopropenyl oxazoline by dehydration in the presence of a strong base.

The reaction described by de Benneville et al. does not provide a method to make oxazolines without alkyl substituents in both 4 positions. Other known reactions require multiple steps and/or expensive reagents. What is needed is a simple process to form either monosubstituted or unsubstituted 2-(1-alkylalkenyl)oxazolines such as isopropenyl oxazoline from readily available materials with a small number of steps.

SUMMARY OF THE INVENTION

The present invention provides a simplified method for synthesizing vinyl oxazolines. In one aspect, the present invention is a process for preparing an N-(2-hydroxyalkyl)-2-alkyl-2-unsaturated-amide comprising contacting:
(1) an alkyl 2-alkyl-2-unsaturated-carboxylate ester:
(2) with a β-aminoalkanol which contains at least one hydrogen bonded to the amine bearing carbon:
(3) in the presence of a catalytic amount of alkali metal hydroxide and/or alkoxide
under conditions such that an N-(2-hydroxyalkyl)-2-alkyl-2-unsaturated-amide is formed.

In a second aspect of the present invention, a 2-(1-alkyl-1-unsaturated) oxazoline with no more than one substituent in the 4 position can be formed by following the procedure outlined above and continuing with a cyclization step:
contacting the N-(2-hydroxyalkyl)-2-alkyl-2-unsaturated-amide in a liquid phase with a catalytic amount of weak Lewis acid in a solvent at elevated temperatures under conditions such that a 2-(1-alkylvinyl) oxazoline is formed.

Oxazolines prepared by the process of the present invention can be polymerized to form useful reactive polymers under conditions described in Tomalia, 2 *Functional Monomers, supra* at 83–89 and de Benneville et al., *Oxazine and Oxazoline Polymers*, U.S. Pat. No. 2,897,182 (July 28, 1959) (commencing at column 10, line 15), which are incorporated herein by reference. The compounds are also useful as ingredients in coatings, textiles, fibers and paper, as antistatic agents, as corrosion inhibitors, as binders for non-woven textiles, and as stabilizers for vinyl halide resins.

DETAILED DESCRIPTION OF THE INVENTION

Processes of the present invention utilize the reaction of a 2-alkyl-2-unsaturated-carboxylate ester. In esters used to practice the invention, the carbon adjacent to the carboxyl group (the 2 carbon) is an olefinic carbon which is also bonded by a single bond to an alkyl group. The alkyl group bonded to the 2 carbon is preferably lower alkyl (when used throughout this document, "lower alkyl" means an alkyl group containing no more than about 6 carbon atoms); more preferably methyl, ethyl, propyl or butyl; more highly preferably methyl or ethyl: and most preferably methyl.

Further groups may be bonded to the other carbon in the olefin moiety (the 3 carbon) as long as they do not destabilize the double bond, are stable under process conditions, and do not interfere with subsequent polymerization of the double bond. Groups attached to the 3 carbon are preferably independently hydrogen or lower alkyl. More preferably, at least one is hydrogen and the other is hydrogen or alkyl. Most preferably, both are hydrogen.

The alkyl moiety bonded to the carboxyl oxygen may be any group capable of transesterification which will not undergo side reactions under reaction conditions. Tertiary alkyl groups are difficult to transesterify, so the carbon bonded to the carboxyl oxygen is preferably secondary or primary; more preferably primary. The alkyl group is preferably one group which, when converted to an alcohol, can be distilled off at a moderate temperature. It is more preferably lower alkyl; more highly preferably ethyl or methyl; and most preferably methyl.

Esters useful in the present invention preferably conform to formula I

R¹ and R² represent groups attached to the 3 carbon, R³ represents the alkyl group attached to the 2 carbon and R⁴ represents the alkyl group bonded to the carboxyl oxygen, as those groups have previously been described. Examples of useful esters include methyl methacrylate, ethyl methacrylate, methyl ethacrylate, methyl 2-methyl-2-butenoate, and homologs thereof. The most preferred ester is methyl methacrylate.

Esters useful in the present invention are known compounds. Some, such as methyl methacrylate, are commercially available. Other esters or carboxylic acids from which they can be derived are prepared by known methods, such as by the reaction of an acetylenic compound with tetracarbonyl nickel [Ni(CO)₄] in the presence of an alcohol. Such methods are described in Jones, "Researches on Acetylenic Compounds. XXII", 1950 *J. Chem. Soc.* 230 (1950); Jones, "Researches on Acetylenic Compounds. XXIX", 1951 *J. Chem. Soc.* 48 (1951); Jones, "Researches on Acetylenic Compounds. XXXI", 1951 *J. Chem. Soc.* 766 (1950), which are incorporated herein by reference. Other routes are reported in March, *Advanced Organic Chemistry* 800-01: 835 (3rd Ed. 1985), which is incorporated herein by reference.

The ester reacts with a β-aminoalkanol. The β-aminoalkanol comprises a primary amine and a hydroxyl group bonded to adjacent paraffinic carbons. The carbon bearing the amine group (the β carbon) may be bonded to one hydrogen atom and one hydrocarbyl substituent or, preferably, to two hydrogen atoms. The carbon bearing the hydroxyl group (the α carbon) may be bonded to two hydrocarbyl substituents or, preferably, to one hydrogen atom and one hydrocarbyl substituent or, more preferably, to two hydrogen atoms. Most preferably, the β-aminoalkanol is 2-aminoethanol (monoethanolamine: MEA). Hydrocarbyl substituents in the β-aminoalkanol are preferably alkyl: more preferably lower alkyl: more highly preferably ethyl or methyl; and most preferably methyl.

β-Aminoalkanols preferably comply with Formula II

wherein R⁵–R⁷ are hydrogen or hydrocarbyl substituents bonded to the paraffinic carbons as previously described. As previously described, R⁷ is preferably hydrogen. More preferably, at least one of R⁵ and R⁶ is hydrogen, and most preferably all of R⁵–R⁷ are hydrogen.

Examples of preferred β-aminoalkanols include 2-aminoethanol, 2-amino-1-propanol, 1-amino-2-propanol, 3-amino-2-butanol and homologs thereof. β-Aminoalkanols are commercially available and can be prepared by known methods, such as the amination of an epoxide as described in March, *Advanced Organic Chemistry* 368–69 (3rd Ed. 1985) and McManus et al., 3 Synth. Comm. 177 (1973), which are incorporated herein by reference.

Ester and aminoalkanol reagents are used in about equimolar amounts in the present invention. Preferably, the excess of one over the other is no more than about 20 percent by mole, more preferably no more than about 10 percent by mole, and most preferably about equimolar.

The process is catalyzed by an alkali metal hydroxide or alkoxide. The catalyst is preferably a hydroxide or lower alkyl alkoxide, and more preferably a methoxide or hydroxide. The alkali metal is preferably lithium, sodium or potassium: and most preferably sodium or potassium.

The catalyst is used in an amount sufficient to catalyze amidation of the ester by the β-aminoalkanol. The concentration of catalyst by mole is preferably at least about 0.1 percent that of the β-aminoalkanol, more preferably at least about 0.5 percent of the β-aminoalkanol, and most preferably at least about 5 percent of the β-aminoalkanol. The concentration of catalyst by mole is preferably at most about 25 percent that of the β-aminoalkanol and more preferably at most about 10 percent that of the β-aminoalkanol. For best efficiency, it is important that the catalyst be added to the β-aminoalkanol before the alkanol is contacted with the ester. Premature contact of the ester with the catalyst can cause Michael addition and polymerization of the ester double bond, thereby lowering selectivity and yields.

It is also preferable to add known polymerization inhibitors. Phenothiazine is effective for this purpose. A composition of phenothiazine and Irganox 1010* (*trademark of CIBA-Geigy Corporation; a hindered phenolic inhibitor) is also effective. Dinitro-sec-butylphenol is also effective. Inhibitors should be used under conditions in which they are known to be effective.

The amidation may be carried out at any temperature and pressure at which the reagents are liquid and the reaction proceeds. The temperature is preferably at least about 0° C., more preferably at least about 20° C. It is preferably less than about 80° C., more preferably at most about 60° C. A temperature too high can contribute to polymerization and a Michael addition across the ester or amide double bond. The pressure is not critical but is preferably about ambient pressure. The optimum reaction time depends upon the temperature of the reaction and may run up to about 24 hours. It is preferably no less than about 2 hours, more preferably no less than about 4 hours. The reaotion may be carried out in air or under inert atmosphere, such as nitrogen or argon. However, certain polymerization inhibitors need oxygen to function, so care should be taken to choose an inhibitor effective under the chosen atmosphere.

The reaction yields an N-(2-hydroxyalkyl)-2-alkyl-2-unsaturated-amide. Substituent groups in the N-(2-hydroxyalkyl) moiety and the 2-alkyl-2-unsaturated-amide moiety are the same as those in the β-aminoalkanol and the ester, respectively. The amide product preferably complies with formula III

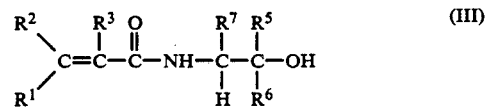

wherein $R^1$, $R^2$, $R^3$, $R^5$, $R^6$ and $R^7$ have the limitations and preferred embodiments previously set out. The amide is preferably N-(2-hydroxyethyl) methacrylamide.

Selectivity to formation of the unsaturated amide, as opposed to the double bond addition products, is preferably at least about 50 percent: more preferably at least about 70 percent; and most preferably at least about 80 percent. Yields of the amide are also preferably at least about 50 percent: more preferably at least about 70 percent; and most preferably at least about 80 percent.

If the amide is to be converted to the corresponding oxazoline, alcohol formed in the amidation step can be drawn off by simple flash distillation under reduced pressure, preferably at about 40° C. or less. Preferably, no further purification is necessary.

Cyclization of the amide to form a 2-(1-alkyl-1-unsaturated)-oxazoline is carried out by contacting the amide with a weak Lewis acid in a liquid phase in a solvent at elevated temperatures. Without intending to be bound thereby, it is theorized that the cyclization occurs through dehydration. The cyclization is a reaction already known for preparing 2-alkyl oxazoline and is described in Litt et al., *Process for the Preparation of Cyclic Amino Ethers*, U.S. Pat. No. 3,681,333 (Aug. 1, 1972); Kaiser, *Process for Preparing 2-Oxazolines*, U.S. Pat. No. 4,203,900 (May 20, 1980); Kaiser, *Preparation of 2-Substituted-2-oxazolines with Organic Zinc Salt Catalysts*, U.S. Pat. No. 4,354,029 (October 12, 1982) and Eisenbraun *Preparation of 2-Oxazolines from N-(2-Hydroxyethyl)amides*, U.S. Pat. No. 3,312,714 (Apr. 4, 1967), which are incorporated herein by reference.

The cyclization can be catalyzed by known catalysts. The preferred weak Lewis acid catalysts are ferric chloride, ferric sulfate, zinc dichloride, zinc acetate or zinc sulfate. The most preferred catalyst is ferric chloride. The reaction is preferably carried out in a solvent which is inert with respect to reactants under reaction conditions, is capable of dissolving both the amide and the catalyst, and is capable of remaining liquid and stable under reaction conditions. Sulfolane is a preferred solvent. Other solvents include glycerol, some glycol ethers, some polyglycols and dibutyl phthalate.

The reaction is run at an elevated temperature. The temperature is preferably at least about 190° C., and more preferably at least about 210° C. The temperature is preferably at most about 250° C., and more preferably at most about 230° C. The temperature is most preferably about 220° C. Small deviations from the optimum temperature (about 10° C. to 20° C.) can cause substantial variation in the yield. The pressure is preferably in a range at which the amide remains liquid under reaction temperatures, but oxazoline and water distill off as they are formed. The maximum pressure is preferably about 400 mm Hg; more preferably about 200 mm Hg; and most preferably about 170 mm Hg. The minimum pressure is preferably about 50 mm Hg; more preferably about 100 mm Hg: and most preferably about 150 mm Hg. If the oxazoline does not distill off quickly, it may polymerize or undergo addition across the double bond through prolonged exposure to high temperature and to the catalyst.

Oxazoline and water distilled from the cyclization reaction are condensed by known methods. For some polymerization utilities, the oxazoline and water line. When it is desirable to separate them, the oxazoline can be removed from the water by extraction from methylene chloride, or by other known methods. The oxazoline is preferably formed in yields of at least about 65 percent based upon the initial amount of β-aminoalkanol: more preferably in yields of at least about 70 percent: and most preferably in yields of at least about 75 percent.

Substituted oxazolines formed in the process of the present invention generally conform with formula IV

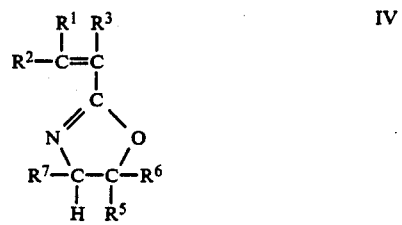

wherein $R^1$, $R^2$, $R^3$, $R^5$, $R^6$, and $R^7$ conform to the limitations and preferred embodiments previously set out. Most preferably, the oxazoline is isopropenyl oxazoline, wherein $R^3$ is methyl and $R^1$, $R^2$ and $R^5$-$R^7$ are all hydrogen.

Oxazolines synthesized by the present process are useful monomers for making known functional polymers. As described in Tomalia, 2*Functional Monomers*, supra, at 83–89, which is incorporated herein by reference, the double bond of the oxazoline can be polymerized by known free radical initiators or by high temperatures to yield a polyalkenyl oxazoline. The oxazoline ring can then be hydrolyzed with alkali or quaternized with methyl iodide to form ion-exchange resins. Such utilities are described in Fazio, *Preparation of Anionic and Cationic Polymers From 2-Oxazolines*, U.S. Pat. No. 4,486,554 (Dec. 4, 1984) and Fazio, *Preparation of Anionic and Cationic Polymers From 2-Oxazolines*, U.S. Pat. No. 4,532,303 (July 30, 1985), which are incorporated herein by reference.

ILLUSTRATIVE EMBODIMENTS

The following examples are for illustrative purposes only and are not to be taken as limiting the scope of either the specification or the claims.

EXAMPLE 1

Preparation of N-(2-hydroxyethyl)methyl acrylamide (HEMA)

A round-bottom flask with a magnetic stirrer is charged with 61.1 g of ethanolamine, 5.4 g of sodium methoxide and 0.4 g of phenothiazine. The contents are stirred. A mixture of 100.1 g of methyl methacrylate and 0.6 g of Irganox 1010* are added with stirring from a dropping funnel over a period of 90 minutes. The temperature is maintained below 40° C. during the addition. The mixture is left to stand at room temperature for about 23 hours. One gram of Irganox 1010* is added and the mixture is stripped on a rotary evaporator at about 60° C. and 8 mm Hg pressure. Product (125 g) is recovered and analyzed by gas chromatography to be 90 percent HEMA. Proton nuclear magnetic resonance spectra show that about 17 mole percent of the product has addition across the double bond and 83 percent is HEMA.

EXAMPLE 2

Preparation of HEMA with Potassium t-Butoxide Catalyst

The procedure of Example 1 is followed except that in place of the sodium methoxide, 7.7 g of potassium t-butoxide is used as the catalyst, and all of the Irganox 1010* (1.6 g) is added to the methyl methacrylate before the addition of the ethanolamine. Product (168.7 g) is recovered which is shown by gas chromatography to be about 74 percent HEMA. Proton nuclear magnetic resonance analysis shows the ratio of HEMA to double bond addition product to be about 71 percent to 29 percent by mole.

EXAMPLE 3

Preparation of HEMA with Sodium Hydroxide Catalyst

Sodium hydroxide pellets (2 g) and ethanolamine (61.1 g) are mixed and heated to 60° C. to form a homogeneous solution. The mixture is cooled to room temperature and 100 g of methyl methacrylate to slowly added over a period of about 60 minutes. After 22 hours at room temperatures, 1.6 g of Irganox 1010* and 0.4 g of phenothiazine are added to the mixture. Methanol is then stripped off at reduced pressure. Product (129.4 g) is recovered which is shown by internal standard gas chromatography to be about 87.4 percent HEMA. Proton nuclear magnetic resonance analysis shows that the ratio of HEMA to double bond addition product is about 83 percent to 17 percent.

EXAMPLE 4

Preparation of HEMA

The procedure as generally set out in Examples 1-3 are followed using the process parameters set out in Table I. Unless otherwise specified, the polymerization inhibitors are Irganox 1010* and 0.4 g of phenothiazine, and are mixed with the methyl methacrylate. Some catalysts are added as solids, indicated by an S, and some in a 25% solution with methanol. Where not specified, the catalyst is added as a solid. Selectivity of the process towards HEMA as opposed to double bond addition products is measured by NMR. The percentage HEMA in the product mixture is also measured by internal standard gas chromatography. (A dash indicates that no chromatography is performed). The results are set out in Table I.

TABLE I

| Temp (°C.) | Mole Ratio[1] | Catalyst | Cata. Conc[2] | Reagent Added[3] | Addition Rate[4] | Run Time (hr) | NMR Selectivity[5] | GC Assay[6] |
|---|---|---|---|---|---|---|---|---|
| 20 | 1 | NaOCH$_3$(25%) | 6 | MEA | S | 24 | 41 | 65 |
| 20 | 1 | NaOCH$_3$(25%) | 6 | MMA | F | 23 | 82 | 91 |
| 20 | 1 | NaOCH$_3$(25%) | 6 | MMA | S | 24 | 81 | 86 |
| 20 | 1 | NaOCH$_3$(25%) | 6 | MEA | S | 24 | 81 | 91 |
| 55 | 1 | NaOCH$_3$(25%) | 6 | MEA & MMA | S | 4 | 70 | 88 |
| 25–60[7] | 1 | NaOCH$_3$(25%) | 0.5 | MMA[8] | S | 20 | 61 | 90 |
| 20 | 1 | NaOCH$_3$(S) | 6 | MMA[8] | S | 23 | 79 | 94[9] |
| 20 | 1 | NaOCH$_3$(S) | 6 | MMA[8] | F | 18 | 83 | 92 |
| 60 | 1 | NaOCH$_3$(S) | 6 | MEA | S | 2 | 78 | 88 |
| 20 | 1 | NaOCH$_3$(S) | 6 | MMA | F | 20 | 82 | 96 |
| 20 | 1 | NaOCH$_3$(S) | 2 | MMA | S | 20 | 71 | 74 |
| 20 | 1 | NaOCH$_3$(S) | 10 | MMA | S | 23 | 83 | 90 |
| 20 | 1 | t-BuOK | 6 | MMA[8] | S | 22 | 77 | — |
| 20 | 1 | NaOCH$_3$(S) | 6 | MMA | S | 25 | 80 | 90 |
| 20 | 1 | NaOCH$_3$(S) | 6 | MMA 10 | F | 12 | 82 | 95 |
| 50–60[7] | 1 | NaOCH$_3$(S) | 6 | MMA 10 | F | 2 | 80 | —[9] |
| 80 | 1 | NaOCH$_3$(25%) | 6 | MMA | S | 2 | 69 | — |
| 25–60[7] | 1.2 | NaOCH$_3$(25%) | 6 | MMA | S | 4 | 80 | 91 |
| 25–56[7] | 1.1 | NaOCH$_3$(25%) | 6 | MMA | S | 5 | 80 | 87 |
| 20 | 1 | NaOH | 5 | MMA* | S | 25 | 83 | —[4] |
| 20 | 1 | NaOCH$_3$(25%) + H$_2$O | 6 | MMA | S | 17 | 83 | — |
| 20 | 0.9 | NaOCH$_3$(25%) | 6 | MMA | S | 23 | 82 | — |

[1] Mole ratio of monoethanolamine (MEA) to methylmethacrylate (MMA).
[2] Mole percent of catalyst per mole of MEA.
[3] Reagent is added to solvent containing catalyst and other reagents.
[4] Rate at which added reagent is added. S = over 2–4 hours. F = over 1–2 minutes.
[5] Selectivity of HEMA over double bond addition product by mole percent determined by NMR.
[6] Percentage of HEMA in sample as determined by internal std. GC after alcohol distilled off.
[7] Temperature raised from low number to high during course of the reaction.
[8] Polymerization inhibitor was phenothiazine only.
[9] Product gelled upon standing.
[10] Inhibitor was phenothiazine & 4-t-butylcatechol.
*Inhibitor added after the run but before stripping.

EXAMPLE 5

Preparation of Isopropenyl Oxazoline

A 250-ml jacketed resin pot with a Teflon ® paddle agitator is fitted with a one-inch diameter 18-inch long vacuum jacketed column, a condenser and a distillation receiver. The reaction is heated by a hot oil unit with temperature control by a thermocouple reading of the oil temperature. The reactor is charged with sulfolane solvent and Lewis acid catalyst. The reactor heated with stirring to 120° C. to dewater the system. The pressure of the system is reduced and the reactor brought to the desired reaction temperature. A feed of HEMA containing some double bond addition product, derived from a process as described in Example 4, is pumped into the system at the specified rate until the specified ratio of HEMA feed to solvent has been added. The reaction is continued until all HEMA is added and until no further isopropenyl oxazoline and water distill from the reactor. The distillate is recovered and analyzed by internal standard gas chromatography. Variable process parameters and results are set out in Table II.

TABLE II

| HEMA Ratio[1] | Catalyst | Temp (°C.) | Feed Rate (ml/min) | Cata/-Solvent[2] | Feed/-Solvent[2] | P mm Hg | Yield[3] |
|---|---|---|---|---|---|---|---|
| 2.4 | ZnCl$_2$ | 210 | 0.68 | 0.060 | 1.75 | 160–70 | 60.6 |
| 2.4 | ZnCl$_2$ | 220 | 0.68 | 0.061 | 1.75 | 150–70 | 67.5 |
| 4 | ZnCl$_2$ | 240 | 0.92 | 0.138 | 2.63 | 325 | 57.0 |
| 3 | ZnCl$_2$ | 220 | 0.47 | 0.131 | 1.75 | 150–70 | 71.1 |
| 2.4 | ZnCl$_2$ | 220 | 0.43 | 0.131 | 1.75 | 150–70 | 74.2 |
| 5 | ZnCl$_2$ | 220 | 0.46 | 0.126 | 1.75 | 150–70 | 70.0 |
| 10 | ZnCl$_2$ | 220 | 0.51 | 0.142 | 1.75 | 150–70 | 75.5 |
| 2.4 | ZnCl$_2$ | 220 | 0.58 | 0.136 | 7.00 | 150–70 | 66.6 |
| 5 | FeCl$_3$ | 220 | 0.91 | 0.140 | 7.65 | 150–70 | 65.6 |

[1] Ratio by mole of HEMA to one mole of double bond addition products in the HEMA feed
[2] Weight ratio
[3] Approximate yield from methyl methacrylate and ethanolamine arrived at by calculating yield as if feed were 100% HEMA

EXAMPLE 6

Preparation of
N-(2-hydroxy-1-propyl)-2-ethyl-2-butenamide

The procedure of Example 3 is repeated using 143 g of ethyl 2-ethyl-2-butenoate in place of the methyl methacrylate, 51 g of 1-amino-2-propanol in place of the ethanolamine, and 4 g of sodium methoxide in place of the potassium t-butoxide. A product is recovered comprising a major portion of N-(2-hydroxy-1-propyl)-2-ethyl-2-butenamide.

What is claimed is:

1. A process for preparing an N-(2-hydroxyalkyl)-2-alkyl-2-unsaturated-amide comprising contacting:
   (1) an alkyl 2-alkyl-2-unsaturated-carboxylate ester;
   (2) with a β-aminoalkanol having a primary amine group and a hydroxy group bonded to adjacent paraffinic carbon atoms which are chosen such that the carbon atom which is bonded to the primary amine moiety is also bonded to at least one hydrogen atom;
   3 in the presence of a polymerization inhibitor and a catalytic amount of alkali metal hydroxide and/or alkoxide;
   (4) at a temperature of less than 80° C.;
   under conditions such that an N-(2-hydroxyalkyl)-2-alkyl-2-unsaturated-amide is formed with a selectivity of at least about 50 percent.

2. The process of claim 1 wherein the concentration of catalyst is at least about 0.1 mole percent of the β-aminoalkanol concentration.

3. The process of claim 2 wherein the alkyl group bonded to the 2 carbon of the ester is a lower alkyl group.

4. The process of claim 3 wherein the ester is a methacrylate ester.

5. The process of claim 2 wherein the carbon atom bearing the amine group in the β-aminoalkanol is bonded to two hydrogen atoms.

6. The process of claim 2 wherein the β-aminoalkanol is 2-aminoethanol, 2-amino-1-propanol, 1-amino-2-propanol, 3-amino-2-butanol, or a homolog thereof.

7. The process of claim 2 wherein the catalyst is added to the β-aminoalkanol prior to contacting the β-aminoalkanol with the ester and wherein the concentration of the alkali metal hydroxide or alkoxide is at least about 0.5 mole percent of the β-aminoalkanol concentration.

8. The process of claim 7 wherein the reaction takes place at between about 20° C. and about 60° C.

9. The process of claim 8 wherein the amide formed is N-(2-hydroxyethyl)methacrylamide.

10. The process of claim 7 wherein the selectivity to the N-(hydroxyalkyl)-2-alkyl-2-unsaturated amide is at least about 70 percent.

11. The process of claim 10 wherein the selectivity is at least about 80 percent.

12. A process for preparing a 2-(1-alkyl-1-unsaturated) oxazoline with no more than one substituent in the 4 position comprising:
   (a) contacting
      (1) an alkyl 2-alkyl-2-unsaturated-carboxylate ester;
      (2) with a β-aminoalkanol having a primary amine group and a hydroxy group bonded to adjacent paraffinic carbon atoms which are chosen such that the carbon atom which is bonded to the primary amine moiety is also bonded to at least one hydrogen atom;
      (3) in the presence of a polymerization inhibitor and a catalytic amount of alkali metal hydroxide and/or alkoxide;
      (4) at a temperature of less than 80° C.;
   under conditions such that an N-(2-hydroxyalkyl)-2-alkyl-2-unsaturated-amide is formed with a selectivity of at least about 50 percent;
   (b) removing alcohol from the product of step (a); and
   (c) contacting the N-(2-hydroxylalkyl)-2-alkyl-2-unsaturated-amide in a liquid phase with a catalytic amount of weak Lewis acid in a solvent at elevated temperatures under conditions such that a 2-(1-alkylvinyl) oxazoline is formed.

13. A process of claim 12 wherein the concentration of catalyst in step (a) is at least about 0.1 mole percent of the β-aminoalkanol concentration the Lewis acid of step (b) is a zinc halide, acetate or sulfate or a ferric halide or sulfate; and the temperature and pressure of step (b) are such that oxazoline and water distill off approximately as they are formed.

14. The process of claim 13 wherein the alkyl group in the 2 position on the ester of step (a) is a lower alkyl group; the catalyst of step (a) is an alkali metal hydroxide or alkoxide; and the temperature of step (b) is about 190° C. to about 250° C.

15. The process of claim 14 wherein the acrylate ester is a methacrylate ester.

16. The process of claim 14 wherein the carbon atom bearing the amine group in the β-aminoalkanol of step (a) is bonded to two hydrogen atoms.

17. The process of claim 14 wherein the aminoalkanol is 2-amino-ethanol, 2-amino-1-propanol, 1-amino-2-propanol, 3-amino-2-butanol, or a homolog thereof.

18. The process of claim 14 wherein the catalyst is added to the β-aminoalkanol in step (a) prior to contacting the β-aminoalkanol with the ester and wherein the concentration of the alkali metal hydroxide or alkoxide in step (a) is at least about 0.5 mole percent of the β-aminoalkanol concentration.

19. The process of claim 14 wherein the reaction of step (a) takes place at between about 20° C. and about 60° C.; and the reaction of step (b) takes place at about 210° C. to about 230° C.

20. The process of claim 19 wherein the oxazoline formed is isopropenyl oxazoline and the pressure of distillation is 100–200 mm Hg.

21. The process of claim 20 wherein the pressure of distillation is about 150 mm Hg to about 170 mm Hg.

22. The process of claim 14 wherein the amide formed in step (a) passes on to step (b) without any purification beyond removal of alcohol formed in step (a).

* * * * *